(12) United States Patent  
Makhlouf

(10) Patent No.: US 9,320,422 B1  
(45) Date of Patent: Apr. 26, 2016

(54) SURGICAL RETRACTOR

(71) Applicant: M Vincent Makhlouf, Glenview, IL (US)

(72) Inventor: M Vincent Makhlouf, Glenview, IL (US)

(*) Notice: Subject to any disclaimer, the term of this patent is extended or adjusted under 35 U.S.C. 154(b) by 449 days.

(21) Appl. No.: 13/730,036

(22) Filed: Dec. 28, 2012

(51) Int. Cl.
*A61B 1/267* (2006.01)
*A61B 1/32* (2006.01)
*A61B 1/00* (2006.01)

(52) U.S. Cl.
CPC .............. *A61B 1/32* (2013.01); *A61B 1/00094* (2013.01)

(58) Field of Classification Search
CPC . A61F 9/00736; A61B 17/56; A61B 17/7011
USPC ........................................................ 600/190
See application file for complete search history.

(56) References Cited

U.S. PATENT DOCUMENTS 4,213,460 A * 7/1980 Weiner .......................... 606/131
6,673,078 B1 * 1/2004 Muncie .............. A61B 17/1697
606/104

* cited by examiner

*Primary Examiner* — Samuel Hanna
(74) *Attorney, Agent, or Firm* — Kelly & Krause, L.P.; W. Dennis Drehkoff

(57) ABSTRACT

A surgical retractor having first and second elongate members with semi-circular distal ends and proximal ends with a coupling area there between for maintaining tissue away from a surgical site. One elongate member is inserted into a surgical site and serves as a template for forming a pocket therein. A second elongate member is connected to the first inside the surgical site and serves as a template for creating the opposed half of the pocket. Relatively large inplant, 14-15 cm are inserted into the pocket.

3 Claims, 2 Drawing Sheets

SURGICAL RETRACTOR

BACKGROUND

1. Field of the Invention

The invention relates to a surgical retractor and more particularly, to a surgical retractor primarily used for insertion of implants in buttock augmentation procedures. The invention also relates to a template used for forming pockets for securing implants.

2. Description of the Prior Art

There has been increasingly more interest and development of retractors and retractor systems that are adaptive for use in small wounds and less invasive procedures. Many of the recent developments are based on traditional types of surgical retractors for open procedures, predominately table-mounted devices of various designs. Many of the devices are cumbersome and are not well adapted for use in small incisions. Traditional hand-held surgical retractors can be modified to fit the contours of small incisions but they often require manual manipulation to maintain a desired placement occupying one hand of the physician or requiring another person to assist the physician during the procedure. Conventional retractors are also positioned in the soft tissue and are levered back to hold the wound open, frequently requiring repositioning if they dislodge, obstructing the physician's view, or interfering with access to the surgical site.

Minimally invasive surgical approaches using relatively small retractors have been applied to orthopedic surgery and other surgical areas for example arthroscopic knee surgery or gall bladder surgery where the affected area is contained within a small region of the body. There has been little effort in designing a surgical retractor for relatively small incisions leading to pockets that are relatively large because of the necessity of holding large implants, for example, typical implants utilized in buttock augmentation that are about two times larger than the opening of the incision. Further, there has been little effort in designing a retractor that can also be used as a template to assist in forming a pocket for the insertion of an implant therein.

In order to be more efficient, the buttock augmentation procedure should have only one incision and, on each buttock, a pocket made substantially the same size as the implant. This improved approach, using a properly designed retractor should encompass as many variations and applications as possible thereby allowing the surgeon to adjust the procedure to accommodate the anatomy and surgical needs of the patient as presented. Therefore, there is a continuing need for an improved buttock retractor that assists in the efficient formation of a properly formed pocket and insertion of an implant.

SUMMARY OF THE INVENTION

One embodiment of the invention is a surgical retractor that displaces tissue away from a surgical site in a body during surgery to expose the surgical site permitting *facile* access for forming a pocket for the implant and the subsequent placement of the implant. One embodiment comprises a surgical retractor having a pair of opposed elongate members each having a distal and a proximal end and a connector located between the proximal and distal ends. The distal ends of both the first elongate members and second elongate members comprise a segment of a circle whose chord lies along a diameter of the circle forming semicircles. Each of the elongate members enter the incision separately to assist in the formation of a pocket for placement of the implant. When the first and second elongate members are connected, the distal ends form a complete circle. A first elongate member is inserted into the incision and with the aid of a cauterizing tool which is moved into the surgical site, the tool forms a pocket for receiving an implant. The first elongate member is positioned in the lower portion of the pocket to be formed creating a semicircular area for about one-half of the pocket. The second elongate member is then inserted into the surgical site and moved to the pocket and placed in the upper half of the pocket where it assists the surgeon in creating a second semicircle opposed to the first so that a complete circle is formed in the pocket. The pocket is created to have a sufficient depth for receiving an implant. A handle connected to the distal and proximal end of the retractor is sufficiently long to allow the surgeon to reach into the surgical site and create the pocket. The handle also serves to measure the distance of between the pocket and incision. This distance is noted and used to calculate the placement of the implant on the opposed buttock. The proximal end of the handle is displaced from an axis running from the handle to the distal end. This is achieved for allowing the surgeon a clear sight line into the surgical incision. In addition, a conventional retractor may be used to retain the fascia and muscle. The conventional retractor may illuminate the surgical site. A vacuum device may also inserted into the surgical site to remove the smoke from the cauterization of tissues. Further, the first and second elongate members have conduits that run from the handle onto the semicircular segments. The conduits have apertures on each semicircular segment. The proximal end of each of the conduits is attached to a vacuum source so that blood may be withdrawn into the apertures and through the conduit away from the surgical site to be collected in the vacuum device.

Another embodiment of the invention is a surgical template wherein the distal ends of the first and second elongated members, when presented in the surgical site each create an opposed arc upon which the cauterizing tool may follow. By this procedure, one-half of the pocket is formed by the cauterizing tool following the arc of the first elongated member. When the distal end of the second elongated member is inserted into the incision and presented in the surgical site, the cauterizing tool follows the arc of the second member thereby completing a circular shape which is substantially the same dimensions of the implant inserted into the pocket. The distal ends of the template when formed into a complete circle are substantially the same size as the implant. The dimensions of the distal ends may be chosen as desired to substantially match the dimensions of the implant and therefore the required pocket.

BRIEF DESCRIPTION OF THE DRAWINGS

Embodiments of the presently disclosed retractor are designed herein with reference to the accompanying drawings, wherein.

DETAILED DESCRIPTION OF THE EMBODIMENTS

Figure 1:
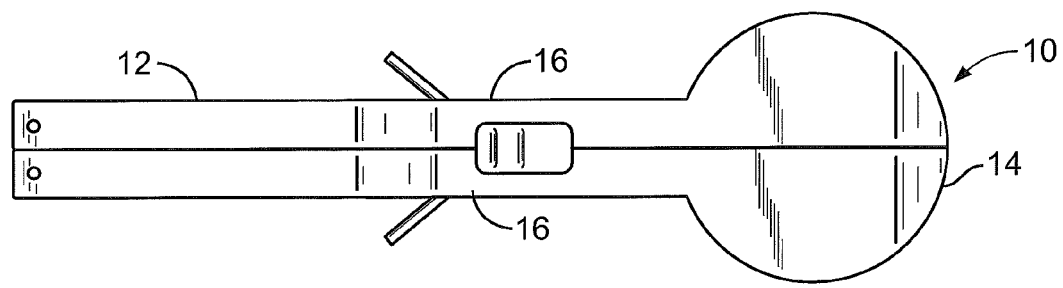
FIG. 1 is a top view of the retractor according to an embodiment of the present disclosure.

Embodiments of the presently disclosed retractor will now be described in detail with reference to the drawings wherein the reference numerals identify similar or identical elements. In the drawings and in the description that follows, the term "proximal," as is traditional, will refer to the end of the retractor which is closest to the operator while the term "distal" will refer to the end of the device which is furthest away from the operator.

Figure 2:
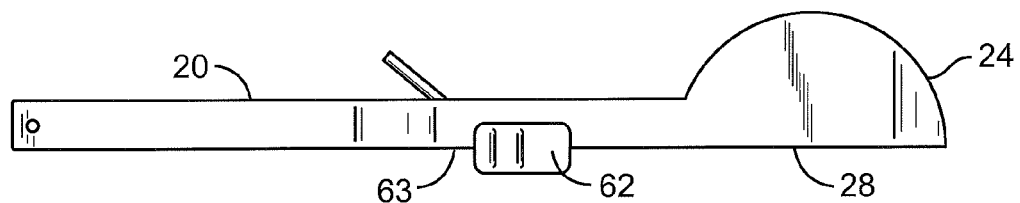
FIG. 2 is a top view of the second elongated member of the retractor of the present disclosure showing the distal end having a segment of a circle whose chord lies along a diameter of the circle.
Figure 3:
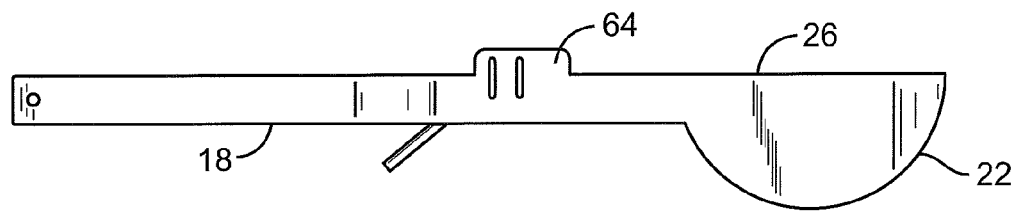
FIG. 3 is top view of a first elongate member of the retractor of the present disclosure having a segment of a circle whose chord lies along a diameter of the circle opposed to the elongate member FIG. 2.

Referring initially to FIGS. 1-3, an embodiment of the presently disclosed retractor is illustrated and generally designated as 10. Retractor 10 includes a proximal end 12 and a distal end 14 with intermediate handles 16 joining handles 18 and 20. First elongate handle 18 is shown in the figures with second elongate handle 20. In addition, first elongate member includes distal end 22 and the second elongate member includes distal end 24. Distal ends 22 and 24 comprise a segment of a circle whose chord lies along a diameter of the circle. The chord of an arc is a straight line joining the two ends of the arc. Chords 26 and 28 are shown respectively on first distal end 22 and second elongated member 24.

Figure 4:
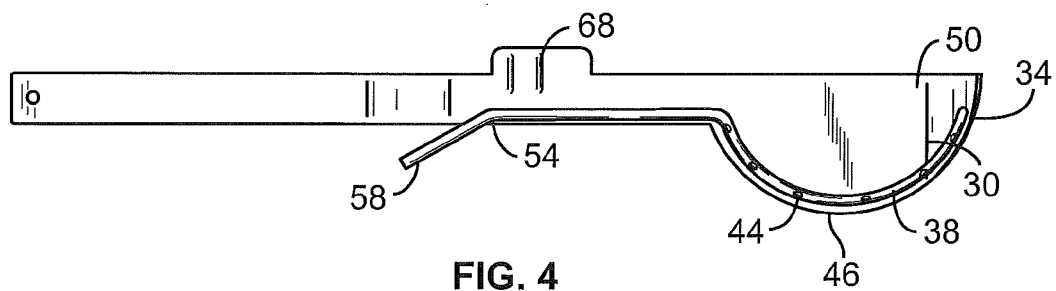
FIG. 4 is a bottom view of the second elongate member shown in FIG. 2.
Figure 5:
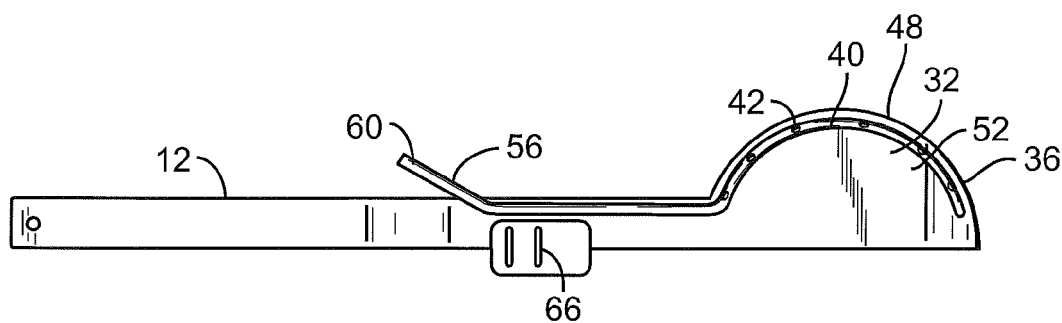
FIG. 5 is a bottom view of the first elongate figure shown in FIG. 3.
Figure 6:
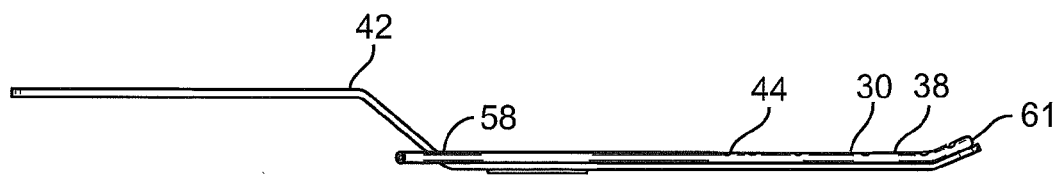
FIG. 6 is a side view of the retractor shown in FIG. 4 exhibiting an edge of a flat surface.

With respect to FIGS. 4-6, FIGS. 4 and 5 show underside 30 and 32 of retractor 10. On the underside distal ends 34 and 36 of the undersides 30 and 32, running towards the proximal end 12 are conduits 38 and 40 having a plurality of apertures 42 and 44 on the distal ends 22 and 24. The contour of the conduits 38 and 40 matches the curvature 38 and 40 at their outside edges 46 and 48 of the semi-circles 50 and 52. At the proximal end 54 and 56 of the conduits 38 and 40 there are wings 58 and 60 which are the distal ends of the conduits that are not aligned with intermediate handle 16 and move away from intermediate handle 16 at an angle so hoses (not shown) can be connected to them. The hoses are connected to a vacuum pump (not shown) that removes blood during the formation of a pocket (not shown) that receives the implant having the desired size and made from either medical grade silicon or adipose tissue taken from the patient.

FIG. 6 is a side view of the retractor in FIG. 4 showing a flat surface, which has underside 30 showing conduit 38, apertures 44 and wing 58. Tip 61 of distal end 22 is curved upward to allow for easy movement within the incision and pocket. Curved handle 42, near proximal end 12 and proximal handles 18 and 20, on an axis running the length of intermediate handle 16 is offset allowing the surgeon to see inside the incision and pocket for manipulating retractor 10. When the first elongate member with distal end 22 and second elongate member including distal end 24 are joined at the chords 26 and 28 as shown in FIG. 1, they form a circle with a flat surface.

In operation for buttocks augmentation, retractor 10 maintains the surgical site, exposes the surgical site and allows access thereto. An incision is made on the skin of the patient above the coccyx, typically about 7 to 8 cm in length. A cauterizing tool, not shown, is used to cut through the fascia. It is also used to begin the formation of a pocket for receiving the implant. When the pocket is of an adequate size for holding the first elongate handle 18 and distal end 22, the distal end 22 is placed against the tissue in the pocket forming a template on the lower side of the pocket. The cauterizing tool burns tissue around distal end 22 forming a semi-circle. At this point, second elongate handle 20 is moved into the incision and distal end 24 is positioned so chords 26 and 28 meet so that the two distal ends 24 and 22 form a circle. The cauterizing tool uses distal end 24 as a guide or template for cutting tissue and, opposed to the lower side of the pocket, completing the formation of a circular pocket of adequate size for the desired implant. As the two elongate members are positioned in the pocket, connectors 62 and 64 are joined so that retractor 10 is stable. The joined intermediate handles 16 and distal ends 22 and 24 assist in the insertion of the implant of the desired size. Typically, the implants are made from medical grade silicon or adipose tissue taken from the patient. The foldable implant may be as large as 14 to 16 cm. in diameter. Conventional retractors and smoke or blood removing devices are also used with retractor 10. As stated, a cauterizing tool is inserted through the incision and begins the formation of a pocket on the opposing buttock. The first elongate handle 18 and distal end 22 are inserted into the partially formed pocket and placed at the top of it. Using the distal end 22 this way, insures the symmetry of the placement of the implants. The cauterizing tool traces the outline of semi-circle. Then, elongate handle 18 with distal end 24 are inserted in the pocket forming a circle. Connectors 62 and 64 are joined in coupling area 63. The connections are made by male 66 and female 68 members that are joined together by the surgeon to stabilize circular distal end, the combination of distal ends 22 and 24 meeting at chords 26 and 28, forming a circle which is the general design of the implant. Implants are placed in the pockets and the procedure is nearly finished. Retractor 10 also serves as a guide for inserting the implants into the pocket. The folded implant is placed on intermediate handle 16 and moved towards distal ends 22 and 24 forming a circle in the pocket. Once in place, retractor 10 is removed from the pocket, one handle 18 or 20 at one time. Not only does retractor 10 assist with the formation of symmetry of the placement of the implants, handles 18 and 20 of retractor 10 serve as a measure to insure the pockets are formed at the desired location away from the coccyx, thus insuring the implants are level and at the required distance from the coccyx.

It is envisioned that the retractor is utilized in an incision of about 7 to 8 cm wherein the implants used in buttocks augmentation are typically 14 to 15 cm in diameter. With the use of retractor 10 a surgeon may utilize an implant about twice the size of the incision. Normal surgical techniques may be used to close the incision.

It is also contemplated that retractor 10 may be manufactured from medical grade metal or composites of metal. The metal may be, but not limited to, aluminum, stainless steel, nickel-titanium, titanium and have a coating, preferably applied by electrostatic spray. A preferred nylon coating is Interpon TP made by Akzo Nobel. The preferred metal for the distal ends is 304 stainless steel; for the conduit, 316 stainless steel.

It will be understood that various modifications may be made to the embodiments of the presently disclosed retractor. Therefore, the above description should not be construed as limiting, but merely examples of embodiments. Those skilled in the art will envision other modifications within the spirit and scope of the present disclosure.

What is claimed is:

1. A surgical retractor for maintaining tissue away from a surgical site in a body during surgery, exposing the surgical site, and permitting access thereto, said surgical retractor comprising:
   a) a pair of opposed first and second elongated members, releasably coupled to each other, each of said first and second elongated members extending along a longitudinal axis from a distal end to a proximal end, each of said first and second elongated members including an elongated handle extending along the longitudinal axis and defining the proximal end of each of the first and second elongated members, each of said first and second elongated members is of a single element, each of the first and second elongated members is defined by opposed flat surfaces connected to each other by opposed side edges extending along the longitudinal axis from the proximal end to the distal end, b) a coupling area on the elongated handle of one of the first and second elongated members and disposed between the distal and proximal ends of each of the first and second elongated members, c) the distal end of the first elongated member is enlarged relative to the elongated handle defining the proximal end of the first elongated member, one of the opposed side edges connecting the opposed flat surfaces of said distal end of the first elongated member is a curved edge along the longitudinal axis and the other one of the opposed side edges connecting the opposed flat surfaces of said distal end of the first elongated member is a straight edge along the longitudinal axis, such that the distal end of the first elongated member defines a segment of a circle and has a semicircular shape, d) the distal end of the second elongated member is enlarged relative to the elongated handle defining the proximal end of the second elongated member, one of the opposed side edges connecting the opposed flat surfaces of said distal end of the second elongated member is a curved edge along the longitudinal axis and the other one of the opposed side edges connecting the opposed flat surfaces of said distal end of the second elongated member is a straight edge along the longitudinal axis, such that the distal end of the second elongated member defines a segment of a circle and has a semicircular shape, e) a connector attached to the elongated handle of the other one of the first and second elongated members aligned with the coupling area so that the first and second elongated handles are to be coupled to each other by engaging the connector with the coupling area, f) the opposed side edges of the elongated handle defining the proximal end of each of the first and second elongated members are straight edges along the longitudinal axis, and one of the straight opposed edges of the elongated handle defining the proximal end of each of the first and second elongated members is aligned with the straight edge of the distal end of each of the first and second elongated members, g) wherein when the first and second elongated handles are coupled to each other at the straight edges of the respective distal ends of the first and second elongated members, the curved edges of the distal ends of both the first and second elongated members define a complete circle with upper and lower flat surfaces; and h) wherein each of the first and second elongated members includes a conduit having a plurality of apertures, and having a contour that matches the curved edge of the distal end of each of the first and second elongated members configured for removing blood under vacuum from the surgical site.

2. The surgical retractor according to claim 1 wherein the distal end of the first elongate member is configured to be inserted into the surgical site.

3. The surgical retractor according to claim 1 wherein the distal end of the second elongate member is configured to be inserted into the surgical site after the first elongate member.

* * * * *